United States Patent [19]

Meilland

[11] Patent Number: Plant 7,408

[45] Date of Patent: Jan. 1, 1991

[54] ROSE PLANE NAMED 'MEIRYPOUX'

[75] Inventor: Alain A. Meilland, Antibes Cedex, France

[73] Assignee: Rotary Rose Company, Litchfield Park, Ariz.

[21] Appl. No.: 422,980

[22] Filed: Oct. 17, 1989

[51] Int. Cl.[5] ..... A01H 5/00

[52] U.S. Cl. ..... Plt./21

[58] Field of Search ..... Plt. 20, 21

*Primary Examiner*—James R. Feyrer

[57] ABSTRACT

A new and distinct variety of Hybrid Tea rose plant is provided having double flowers of original currant Red color, very even, without the white veins. The seed parent of the new variety resulted from the pollination of the variety MISTER LINCOLN by the variety Meiluminac. The male parent of the new variety was the variety Karl Herbst. The new variety is particularly suited for use in the beautification of parks and gardens.

1 Drawing Sheet

BACKGROUND OF THE INVENTION

The object of the present invention is a variety of rose-plant of the Hybrid Tea Class which is distinguished from already known varieties in this class and in this color range by the following features:

very nice erect habit, well organized and balanced plants double flower of original Currant Red color that doesn't fade plant that tolerates heat conditions very well very even color of the petals; without the white veins commonly found in most other red varieties Because of the above-mentioned characteristics, the present invention responds to the needs of the horticultural industry for all uses and, most particularly for park and garden decoration.

The variety, object of the present invention owes its origin to an artificial pollination made between two parents whose genetic background indicated that offspring of the union would exhibit the desired characteristics.

The rose-plant chosen as female parent (seed-parent) was the product of the pollination of the variety Mister Lincoln by The variety: Meiluminac.

The one chosen as a male parent (pollen) was the variety: Karl Herbst

The operation of artificial pollination thus made is expressed by the following:

(Mister Lincoln × Meiluminac) × Karl Herbst

The seeds resulting from the above pollination were sown and small plants were obtained, physically and biologically distinct one from the other.

After eliminating all the deficient or abnormal subjects or those whose characteristics deviated from those which were the object of the research, propagation of the remaining plants was undertaken.

From that point the selective study of the remaining varieties was undertaken. In the course of this study all the varieties were systematically eliminated, except one, the one closest to the desired goal.

This rose-plant produced double flowers of original Currant Red color which did not fade. The plant was also tolerant to heat. The flowers showed a very nice shape, perfect for exhibition, and the petals showed a very even color.

Technical tests (propagation by budding, grafting and cuttage) were then undertaken with the aim of verifying the behavior and the productiveness of the created variety. The results were conclusive and stressed the importance of this variety with a view to its industrial exploitation for all uses and most particularly for park and garden decoration.

The characteristics and properties of the new variety obtained as shown above, are stable and are transmissible by all forms of asexual propagation. The new variety is called:

The Meirypoux variety.

SUMMARY OF THE INVENTION

A new industrial product, a variety of rose plant of the Hybrid Tea Class characterized by:

(1) From physical point of view, the plant has medium green foilage and adult wood has an upright habit. The flower is double with original Current Red coloration, with a perfect shape ideal for exhibition. The plant also tolerates the heat really well and the flowers do not face.

(2) From a biological point of view, this rose plant has quite vigorous vegetation, abundant and continual blooming and is not particularly affected by cryptogamic diaeases. Its flowers last a long time and their petals drop off cleanly.

BRIEF DESCRIPTION OF THE PHOTOGRAPH

The accompanying drawings show as nearly true as it is reasonably possible to make the same in color illustration of this character.

The drawing shows defoliated canes with thorns (top left); new terminal growth (bottom left); fully expanded flower, expanding flower, and unopened flower bud and detached petals (center top to bottom); the top of a seven leaflet foliole (top right); and, the bottom of a five leaflet foliole (bottom right).

DETAILED DESCRIPTION

The following descriptive characteristics of the new variety were taken from two (2) year old plants grown in container, budded on Dr. Huey in West Grove, Pa., and observed in April in the greenhouse.

The chart used for the identification of the colors is the one of The Royal Horticultural Society (R.H.S. Color Chart). The terminology which precedes the numbered references proper to this chart has been added to qualify, in common terms, the corresponding colors.

Class: Hybrid Tea.

Plant:

*Height.*—110 cm.

*Habit.*—Upright.

Branches:

*Young stems:* 138B Green Group, stained with reddish. Adult wood: 147B Yellow Green. Thorns — Size: Large. Quantity: Moderately numerous. Color: Young Stems: Light green (yellowish) green). Adult Wood: Reddish.

Leaves:

*Stipules.*—Adnate, pectinate, wide and dented.

*Petiole.*—Upper side: Young leaf — narrow, reddish. Adult leaf — medium green strongly stained reddish with glandular edges. Under side: Medium green, smooth.

*Folioles.*—Number: 3, 5 and 7. Sometimes the lower pair of leaflets is incomplete. Shape: Elliptic. Serration: Single and regular. Texture: Consistent. General effect: Fairly dense, medium green, dull foliage. Color: Young foliage: Upper side: 147A Green Group stained with reddish. Under side: 147A Green Group strongly stained with reddish. Adult Foliage: Upper side: 137A Green Group. Under side: 146A Green Group.

INFLORESCENCE

Number of flowers: Usually 1 flower per stem.

Peduncle:

*Length.*—6 cm on average.

Sepals:

*Upper side.*—Greenish, tomentose, strongly stained reddish.

Bud:

*Shape.*—Pointed.

*Length.*—3.5 cm on average.

*Size.*—Medium to large.

*Color.*—Upper side: Currant Red ranging near 46A Red Group strongly effused with black, especially on the outer petals. Under side: Currant Red 46A Red Group and lighter.

Flower:

*Shape.*—Cuplike, well shaped, high centered.

*Diameter.*—12 to 13 cm.

*Color.*—When opening: Upper side: 47B Red Group. Under side: Currant Red 46A Red Group on the outside petals turning 45B on the inside, the outer petals are strongly stained with black. When blooming: Upper side: 45B Red Group. Under side: Cardinal Red 53D, Red Group. When finishing blooming: Upper side: 45B Red Group turning 45C. Under side: Cardinal Red 53D Red Group.

Fragrance: None.

Lasting quality: Long lasting.

Petals:

*Shape.*—Outer: Oval. Inner: Oval.

*Texture.*—Consistent.

*Number.*—27 on average.

*Cleaning.*—Good.

Stamens:

*Number.*—153.

*Anthers.*—Normal strawlike.

*Filaments.*—Irregular in height, bright yellow at base turning orange then orange-red near filaments. Uniformly located around receptacle.

Pistils:

*Number.*—50 outside — 45/50 bundled together inside.

*Stigmas.*—Normal ochre.

*Style.*—Irregular in height, the inner pistils are smaller/outer.

*Receptacle.*—Light medium green. Smooth, wide, it is in its longitudinal section, in the shape of a wide pitcher.

DEVELOPMENT

Vegetation: Fairly vigorous.

Blooming: Continuous throughout seasons.

Aptitude to bear fruits: Moderate.

Resistance to frost: Good.

Resistance to diseases: Normal.

I claim:

1. A new and distinct variety of Hybrid Tea rose plant, named 'Meirypoux', as described and illustrated.

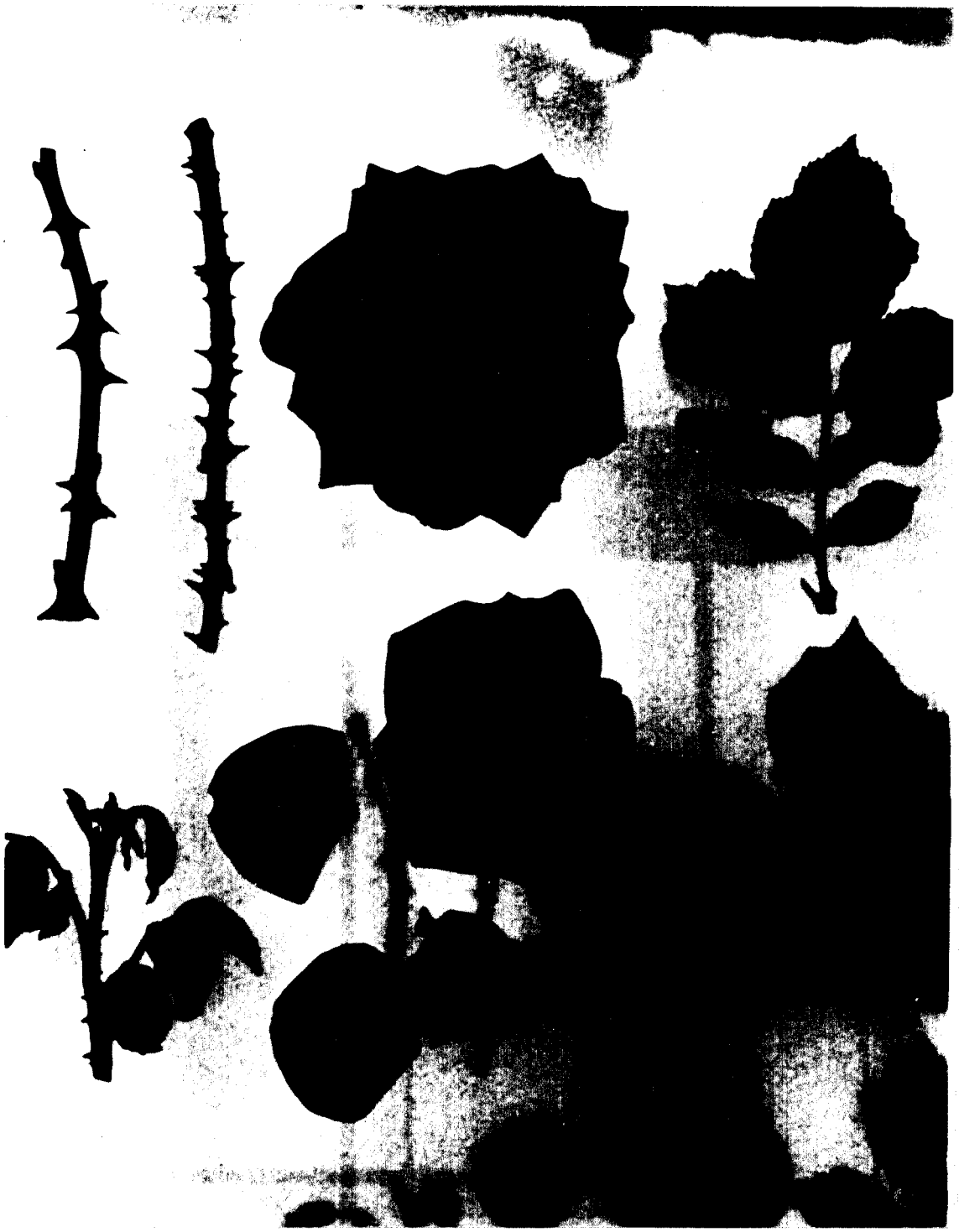

* * * * *